United States Patent [19]

Hadley et al.

[11] 4,213,983

[45] Jul. 22, 1980

[54] TREATING GASTRO-INTESTINAL DISORDERS AND EMESIS WITH N-(HETEROCYCLIC SUBSTITUTED) BENZAMIDES

[75] Inventors: Michael S. Hadley, Sawbridgeworth; Eric A. Watts, Harlow, both of England

[73] Assignee: Beecham Group Limited, England

[21] Appl. No.: 845,027

[22] Filed: Oct. 25, 1977

[30] Foreign Application Priority Data

Nov. 5, 1976 [GB] United Kingdom ............... 46105/76

[51] Int. Cl.² .................. A61K 31/495; C07D 471/04
[52] U.S. Cl. ............................... 424/250; 260/239 B; 424/244; 544/344; 260/239 BC; 260/326.25; 260/326.27; 424/267; 424/274; 544/349; 546/93; 546/94; 546/95; 546/138
[58] Field of Search ............ 260/293.53, 293.54, 260/239 B, 326.27, 239 BC, 326.25; 544/349, 344; 546/138, 93, 94, 95; 424/250, 244, 267, 274

[56] References Cited

U.S. PATENT DOCUMENTS

| | | | |
|---|---|---|---|
| 3,176,017 | 3/1965 | Freed | 544/349 |
| 3,357,978 | 12/1967 | Thominet | 260/326.25 |
| 3,452,025 | 6/1969 | Hansen et al. | 546/95 |
| 3,692,791 | 9/1972 | Potoski et al. | 260/293.53 |

FOREIGN PATENT DOCUMENTS 2037661 8/1971 Fed. Rep. of Germany .

OTHER PUBLICATIONS

Migrdichian, V., *Organic Synthesis*, vol. 1, Reinhold Pub. Corp., New York, 1957, pp. 368–369.

*Primary Examiner*—John M. Ford
*Assistant Examiner*—Richard A. Schwartz
*Attorney, Agent, or Firm*—Jacobs & Jacobs

[57] ABSTRACT

Compounds of the formula (I), and their pharmaceutically acceptable salts:

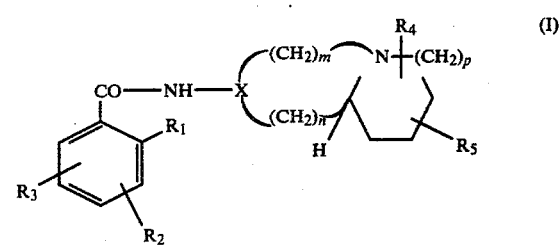

wherein:

$R_1$ is a $C_{1-6}$ alkoxy group;

$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino aminocarbonyl or aminosulphone optionally substituted by one or two $C_{1-6}$ alkyl groups, $C_{1-6}$ alkylsulphone or nitro groups;

X is either a nitrogen atom, in which case m+n is 3 to 5, m is 2 to 4, n is 1 to 3; or X is CH in which case m+n is 2 to 5, m is 1 to 5, and n is 0 to 4;

p is 0 to 3;

$R_4$ is hydrogen, $C_{1-6}$ alkyl, phenyl or phenyl-$C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; are useful for treating disorders of the gastro-intestional function and for treating emesis.

116 Claims, No Drawings

TREATING GASTRO-INTESTINAL DISORDERS AND EMESIS WITH N-(HETEROCYCLIC SUBSTITUTED) BENZAMIDES

This invention relates to novel substituted benzamides having useful pharmacological properties, to pharmaceutical compositions containing them, and to a process for their preparation.

N-(2-Diethylaminoethyl)-2-methoxy-4-amino-5-chlorobenzamide and 1-ethyl-2(2-methoxy-5-sulphamoylbenzamidomethyl) pyrrolidine are commercially available products having useful pharmacological activity such as the ability to regulate the gastro-intestinal function and anti-emetic activity. Both these drugs contain a specifically substituted benzene ring, and at the present time it is believed that only these two structures possess sufficient activity to be of real use to the medical profession in this area of therapy.

It has now been found that a certain class of substituted benzamides has useful pharmaceutical activity. For example compounds within this class may be used for treatment of disorders of the gastro-intestinal function, such as retarded gastric emptying, dyspepsia, flatulence, oesophagal reflux, peptic ulcer and the like; and/or for the treatment of emesis.

Accordingly, the present invention provides a compound of the formula (I), and pharmaceutically acceptable salts thereof:

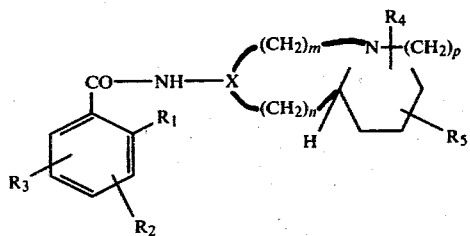

wherein:

$R_1$ is a $C_{1-6}$ alkoxy group;

$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminocarbonyl or aminosulphone optionally substituted by one or two $C_{1-6}$ alkyl groups, $C_{1-6}$ alkylsulphone or nitro groups;

X is either a nitrogen atom, in which case m+n is 3 to 5, m is 2 to 4 and n is 1 to 3; or X is CH in which case m+n is 2 to 5, m is 1 to 5, and n is 0 to 4;

p is 0 to 3;

$R_4$ is hydrogen, $C_{1-6}$ alkyl, phenyl or phenyl-$C_{1-6}$ alkyl, either of which phenyl moiety maybe substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen.

A group of compounds within formula (I) are those wherein;

$R_1$ is a $C_{1-6}$ alkoxy group;

$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminosulphone, aminosulphone substituted by one or two $C_{1-6}$ alkyl groups, $C_{1-6}$ alkylsulphone or nitro groups;

X is a nitrogen atom, in which case m is 2 and n is 1; or X is CH in which case m+n is 2 or 3, and m is 1, 2 or 3 and n is 0, 1 or 2;

p is 0 or 1;

$R_4$ is hydrogen, $C_{1-6}$ alkyl, phenyl or phenyl-$C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; and salts thereof.

Suitable examples of the group $R_1$ include methoxy, ethoxy and n- and iso-propoxy. Preferably $R_1$ is a methoxy group.

Suitable examples of the groups $R_2$ and $R_3$ include the following groups: hydrogen, chlorine, bromine, $CF_3$, hydroxy, methoxy, ethoxy, n- and iso-propoxy, n- and sec- and tert-butoxy, acetyl, propionyl, butyryl, amino, amino substituted by one or two methyl, ethyl, n- or iso-propyl, n-, sec- or tert-butyl groups, acetylamino, propionylamino, butyramino, aminosulphone, aminosulphone substituted by one or two methyl, ethyl, n- or iso-propyl, n-, sec- or tert-butyl groups, and methyl, ethyl and n- and iso- propylsulphones, and nitro, $R_2$ and $R_3$ may also be aminocarbonyl, optionally substituted as for an aminosulphone group.

Particularly suitable $R_2$ and $R_3$ groups include hydrogen, halogen, amino, and substituted amino as defined.

It is generally preferred that $R_2$ is in the 4- position relative to the carbonyl side chain for greater activity in the resultant compound of the formula (I). For the same reason it is generally preferred that $R_3$ is in the 5- position relative to the carbonyl side chain.

Particularly preferred $R_2$ groups include 4-amino and 4-(substituted amino) as defined. Preferably $R_2$ is 4-amino. Particularly preferred $R_3$ groups include 5-halo, such as 5-chloro.

Suitable examples of $R_4$ include hydrogen, methyl, ethyl, n- and iso-propyl, n-, sec- and tert-butyl; phenyl, phenyl methyl, phenyl ethyl, phenyl-n-propyl, phenyl-iso-propyl, phenyl-n-, sec- and tert-butyl, any of which phenyl moieties maybe substituted by $C_{1-6}$ alkyl, $C_{1-6}$ alkoxy, $CF_3$ or halogen. Suitable examples of such optional phenyl substituents include methyl, ethyl, n- and iso-propyl, n-, sec- and tert-butyl; methoxy, ethoxy, n- and iso-propoxy; $CF_3$, fluoro, chloro or bromo.

Preferred examples of $R_4$ include hydrogen; methyl; phenyl and benzyl. Often $R_4$ will substitute the carbon atom that is adjacent to the nitrogen atom in the ($R_4/R_5$ substituted) ring.

When $R_4$ and $R_5$ represent a fused benzene ring, suitable optional substituents of that fused benzene ring, include methyl, ethyl, n- and iso-propyl, n-, sec- and tert-butyl; methoxy, ethoxy and n- and iso-propoxy; $CF_3$, fluoro, chloro and bromo.

The pharmaceutically acceptable salts of the compound of the formula (I) include acid addition salts with conventional acids such as hydrochloric, hydrobromic, phosphoric sulphuric, citric, tartaric, lactic and acetic acid and the like.

The pharmaceutically acceptable salts of the compounds of the formula (I) also include quaternary ammonium salts. Examples of such salts include salts with compounds such as $R_6$-Y wherein $R_6$ is $C_{1-6}$ alkyl, phenyl-$C_{1-6}$ alkyl or $C_{5-7}$ cycloalkyl, and Y is an anion of an acid. Suitable examples of $R_6$ include methyl, ethyl and n- and iso-propyl; and benzyl and phenyl ethyl. Suitable examples of Y include the halides such as chloride, bromine and iodide..

From the aforesaid it will be seen that suitably the moiety of the formula (IV):

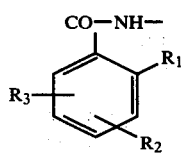

in a compound of the formula (I) will have the structure (V):

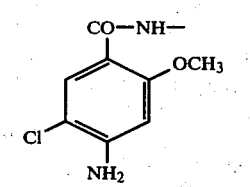

Similarly, when X is nitrogen, the moiety of the formula (VI):

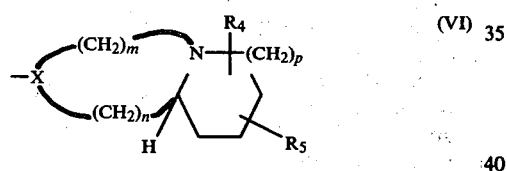

in a compound of the formula (I) can suitably have the structure (VII)

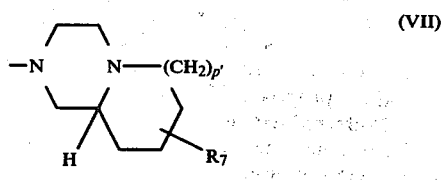

wherein p' is 0 or 1 and $R_7$ is hydrogen; $C_{1-6}$ alkyl; phenyl or phenyl-$C_{1-6}$-alkyl, either of which phenyl moiety maybe substituted by $C_{1-6}$ alkyl, $C_{1-6}$ alkoxy, $CF_3$ or halogen.

Suitable and preferred examples of $R_7$ include those listed hereinbefore for $R_4$. Often $R_7$ will substitute the carbon atom that is adjacent to the nitrogen atom in the ($R_7$ substituted) ring.

Preferably p' is 1.

Also, when X is nitrogen, the moiety of formula (VI) as defined, in a compound of formula (I) can suitably have the structure (VIII), (IX) or (X):

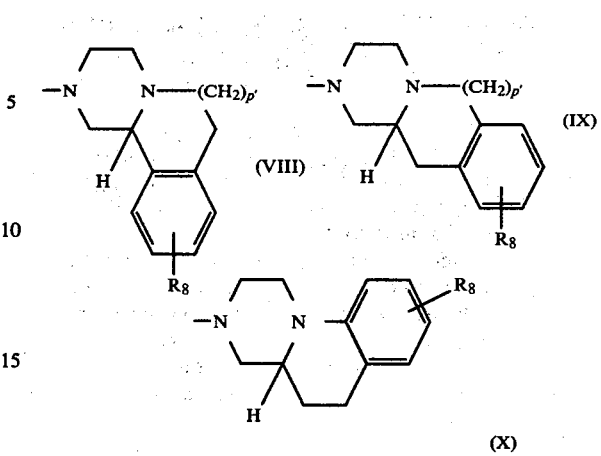

wherein p' is 0 or 1, and $R_8$ is hydrogen, $C_{1-6}$ alkyl, $C_{1-6}$ alkoxy, $CF_3$ or halogen.

p' is preferably 1 in formulae (VIII) and (IX).

Suitable examples of $R_8$ include hydrogen and the groups listed hereinbefore as suitable optional substituents for the fused benzene ring that can be formed by $R_4$ and $R_5$ and the carbon atoms to which they are attached in formula (I).

When X is CH, the moiety of formula (VI), as defined in a compound of formula (I), can have the structure (XI)

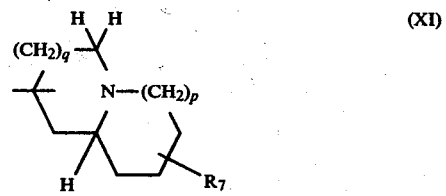

wherein q is 0 to 3, p is 0 to 3, and $R_7$ is as defined in formula (VII).

Suitably q is 0 or 1, and p is 0 or 1, in formula (XI).

When p is 0 or 1, q may also suitably be 2.

Preferably q and p are 1 in formula (XI). Suitable and preferred groups $R_7$ are as described hereinbefore. Often $R_7$ will substitute the carbon atom that is adjacent to the nitrogen atom in the ($R_7$ substituted) ring.

Most suitably in formula (XI) $R_7$ is hydrogen.

When X is CH, the moiety of formula (VI), as defined in a compound of formula (I), can also suitably have the structures (XII), (XIII) or (XIV).

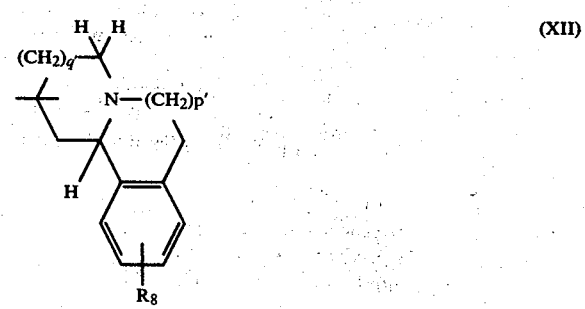

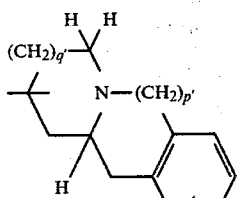

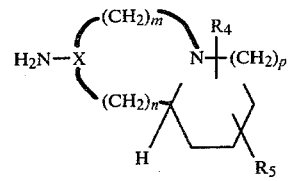

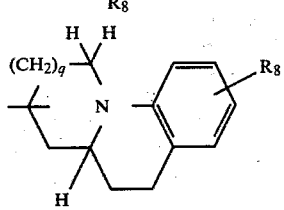

wherein q' is 0 or 1, p' is 0 or 1 and R₈ is as defined.

q' and p' are preferably 1 in formulae (XII), (XIII) and (XIV).

Suitable examples of R₈ are as hereinbefore described.

When q' is 1 in the moieties of formulae (XI), (XII), (XIII) and (XIV), these moieties are preferably substituted at the 4 position relative to their nitrogen atoms by the moieties of formula (IV) as defined.

Particularly suitable examples of compounds of the invention include those specifically prepared in the following Examples.

Other specific examples include:

4-Amino-5-chloro-2-methoxy-N-(9-decahydro-pyrid-[1,2-a]-azepinyl) benzamide.

4-Amino-5-chloro-2-methoxy-N-(8-decahydro-pyrid-[1,2-a]-azepinyl) benzamide.

4-Amino-5-chloro-2-methoxy-N-[2-(6H-benzo[b]-quinolizine-1,2,3,4,11,11a-hexahydro)]-benzamide.

4-Amino-5-chloro-2-methoxy-N-(6-phenyl-2-quinolizidinyl)-benzamide.

It will of course be realised that the compounds of the formula (I) have asymmetric centres, and thus are capable of existing in an number of stereoisomeric forms. The invention extends to each of these stereoisomeric forms, and to mixtures thereof. The different stereoisomeric forms maybe separated one from the other by the usual methods.

The invention also provides a process for the preparation of a compound of the formula (I), which process comprises reacting an acid of the formula (XV):

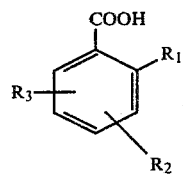

or a reactive derivative thereof, with a compound of the formula (XVI)

the variable groups being as defined in formula (I); and thereafter if desired or necessary converting a group R₂ or R₃ in the thus formed compound of the formula (I) to another group R₂ or R₃.

'Reactive derivative' when used herein means a derivative of the compound (XV) which can be reacted with the compound (XVI) to form an amido linkage between the acid groups of the compound (XV) and the amino group of the compound (XVI).

Often this reactive derivative will be the acid halide, such as the acid chloride, of the acid (XV). In such cases, the reaction will normally be carried out in the inert solvent, preferably in the presence of an acid acceptor. The inert solvent can be any solvent inert to both reactants such as benzene, toluene, diethylether and the like. The acid acceptor is suitably an organic base such as a tertiary amine e.g. triethylamine, trimethylamine, pyridine and picoline, or an inorganic acid acceptor, such as calcium carbonate, sodium carbonate, potassium carbonate and the like. It should also be noted that it is possible to use certain acid acceptors as the inert solvent, for example organic bases.

Another useful reactive derivative of the acid (XV) that may be used is an acid ester, such as a methyl, ethyl, propyl or butyl ester, in which case the reaction is normally carried out by heating the reactants together in an inert solvent such as ethylene glycol.

The reaction may also be carried out by forming an anhydride of the acid (XV) in the usual manner, and reacting that with the compound (XVI)-normally a conventional mixed anhydride will be used; or by reacting the acid (XV) and the compound (XVI) in the presence of a dehydrating catalyst such as a carbodiimide, for example dicyclohexyl carbodiimide.

The intermediates of formula (XV) are either known compounds or can be prepared by analogous processes to known compounds.

The intermediates of formula (XVI), wherein X is CH, may be prepared by reduction of an oxime of the formula (XVII):

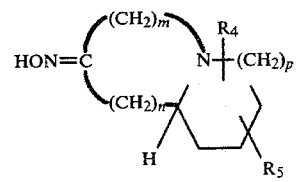

This reduction is carried out with a suitable reducing agent, such as lithium aluminium hydride in solvent such as ether, tetrahydrofuran and the like. Normally a LiAlH₄ reduction will be carried out at a temperature of 25°–70° C. Catalytic hydrogenation may also be used.

The oximes of the formula (XVII) may themselves be prepared from ketones of the formula (XVIII):

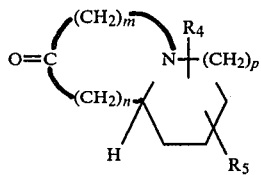

(XVIII)

by reaction with hydroxylamine. This reaction is usually carried out by using the hydroxylamine in the form of an acid addition salt, such as the hydrochloride, in a suitable solvent such as pyridine, and at reflux temperatures. The ketones of formula (XVIII) are either known compounds or may be prepared by procedures similar to those used for known compounds.

The intermediates of the formula (XVI), wherein X is N, may be prepared by reduction of a N-nitroso compound of the formula (XIX):

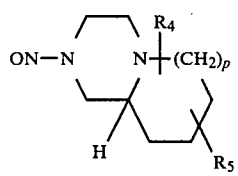

(XIX)

This reduction is carried out using a suitable reducing agent such as lithium aluminium hydride in a solvent such as ether, tetrahydrofuran and the like, normally at temperatures of 25° to 70° C.

The N-nitroso compounds of the formula (XIX) can be prepared from amines of the formula (XX):

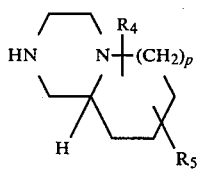

(XX)

by conventional methods. These include reaction with sodium nitrite in dilute hydrochloric acid, or the like. The amines of formula (XX) are either known compounds or may be prepared by procedures similar to those used for known compounds.

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_6Y$ as defined. This reaction is suitably carried out in an appropriate solvent such as acetone, methanol, ethanol, dimethylformamide and the like, at ambient or raised temperature and pressure.

The interconversion of suitable groups $R_2$ and $R_3$ after formation of a compound of the formula (I) may be carried out by conventional methods. By way of example, nitro groups may be reduced to amino groups in the normal manner, and acylamino groups may be converted to amino also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen. Accordingly it will be realised that compounds of the formula (I) containing a $R_2$ or $R_3$ group which is convertible to another $R_2$ or $R_3$ group are useful intermediates, and as such form an important aspect of the invention.

The compounds of the formula (I) have useful pharmaceutical properties. The invention therefore also provides a pharmaceutical composition comprising a compound of the formula (I) or a pharmaceutically acceptable salt thereof, together with a pharmaceutically acceptable carrier. Such compositions may be adapted for oral or parenteral administration, and as such may be in the form of tablets, capsules, syrups, reconstitutable powders, injectable and infusable solutions or suspensions and the like. The compositions may also be in the form of suppositories and the like. Normally orally administrable compositions are preferred.

The invention further provides a method of treatment of maladies in humans comprising the administration of an effective amount of a compound of the formula (I) or a pharmaceutically acceptable salt thereof. The 'effective amount' will depend in the usual way on a number of factors such as the nature and severity of the malady to be treated, and the actual compound used. Usually we have found that a dose of 0.1 to 50, suitably 1 to 4 mg/kg per day is quite sufficient to achieve a satisfactory treatment.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the invention:

EXAMPLE 1

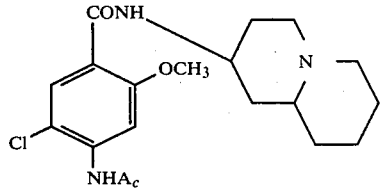

4-Acetylamino-5-chloro-2-methoxy-N-(2-quinolizidinyl)-benzamide

A mixture of 2-quinolizidone (10 g) and hydroxylamine hydrochloride (10 g) in ethanol (50 ml) and pyridine (5 ml) was heated with stirring at reflux for 1 hour. It was then cooled, the solvent evaporated and water and ethyl acetate added to the residue. After basification the organic layer was separated, dried over magnesium sulphate and evaporated to give the oxime (10 g) of 2-quinolizidone as a mixture of isomers.

The oxime (7.1 g) was placed in an extraction thimble of a Soxhlet apparatus and lithium aluminum hydride (3.24 g) and ether (250 ml) in the flask. The mixture was heated at reflux for 24 hours, excess lithium aluminium hydride destroyed and the ethered extract concentrated to give crude 2-amino-quinolizidine (5.8 g) as an oil.

4-Acetylamino-5-chloro-2-methoxy-benzoic acid (9.2 g) was heated at 50° C. with thionyl chloride (100 ml) for 30 minutes. The solution was evaporated, benzene added and evaporated again. The crude acid chloride was dissolved in benzene (300 ml) and triethylamine added (20 ml) followed by 2-amino-quinolizidine (5.8 g). After 30 minutes, dilute sodium hydroxide was added and the mixture extracted with ether. The ethereal extract was dried and evaporated. Recrystallisation of the residue from ethyl acetate—light petroleum afforded one of the isomers of 4-acetylamino-5-chloro-2-methoxy-N-(2-quinolizidinyl)-benzamide (5 g), m.p. 203°–4°.

EXAMPLE 2

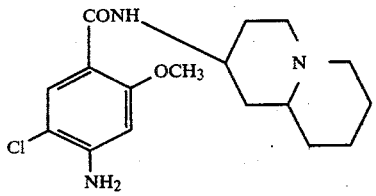

4-Amino-5-chloro-2-methoxy-N-(2-quinolizidinyl)-benzamide (Compound 2)

Hydrolysis of 4-acetylamino-5-chloro-2-methoxy-N-(2-quinolizidinyl)-benzamide (600 mg) with potassium hydroxide (500 mg) in ethanol (10 ml) and water (2 ml) at reflux for 4 hours followed by isolation through ether afforded one of the isomers of 4-amino-5-chloro-2-methoxy-N-(2-quinolizidinyl)-benzamide (400 mg), m.p. 175°–8°.

EXAMPLE 3

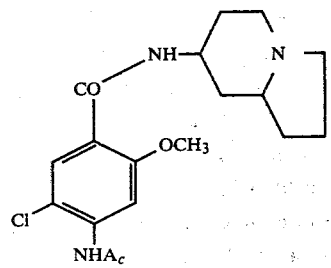

4-Acetylamino-5-chloro-2-methoxy-N-(7-octahydro-indolizinyl)-benzamide.

By a procedure similar to that described in example 1, from 7-octa-hydro-indolizinone, one of the isomers of 4-acetylamino-5-chloro-2-methoxy-N-(7-octahydro-indolizinyl)-benzamide was isolated by chromatography on alumina (deactivated by addition of 10% water) eluting with progressively graded mixtures of dichloromethane and chloroform.

EXAMPLE 4

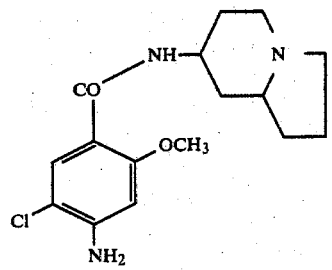

4-Amino-5-chloro-2-methoxy-N-(7-octahydro-indolizinyl)-benzamide

By a procedure similar to that described in example 2, the compound of example 3 was hydrolysed to give one of the isomers of 4-amino-5-chloro-2-methoxy-N-(7-octahydro-indolizinyl)-benzamide (75%), m.p. 193°–4°

EXAMPLE 5

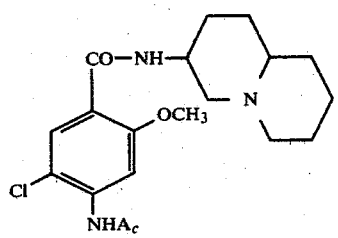

4-Acetylamino-5chloro-2-methoxy-N-(3-quinolizidinyl)-benzamide.

By a procedure similar to that described in example 1, from 3-quino lizidinone, one of the isomers of 4-acetylamino-5-chloro-2-methoxy-N-(3-quinolizidinyl)-benzamide, m.p. 211°–2° was obtained after recrystallisation from ethyl acetate.

EXAMPLE 6

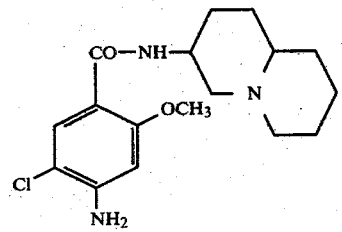

4-Amino-5-chloro-2-methoxy-N-(3-quinolizidinyl)-benzamide

By a procedure similar to that described in example 2, the compound of example 5 was hydrolysed to give one of the isomers of 4-amino-5-chloro-2-methoxy-N-(3-quinolizidinyl)-benzamide, m.p. 207°–8°, after recrystallisation from ethyl acetate-light petroleum.

EXAMPLE 7a, 7b

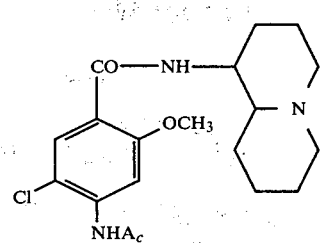

4-Acetylamino-5-chloro-2-methoxy-N-(1-quinolizidinyl)benzamide

By a procedure similar to that described in example 3, from 1-quino lizidinone, both isomers of 4-acetylamino-5-chloro-2-methoxy-N-(1-quinolizidinyl)-benzamide were isolated by chromatography. The more polar isomer (63%) had m.p. 219°–20° and the less polar isomer (37%) had m.p. 173°–4°.

EXAMPLE 8a, 8b

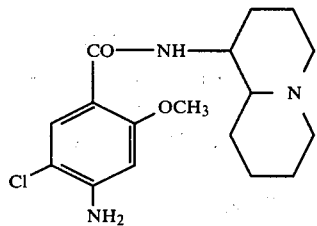

4-Amino-5-chloro-2-methoxy-N-(1-quinolizidinyl)-benzamide

By a procedure similar to that described in example 2, the two isomers of example 8 were individually hydrolysed. The two isomers of 4-amino-5-chloro-2-methoxy-N-(1-quinolizidinyl)-benzamide were isolated, the more polar (example 8a) having a m.p. 152°–5° and the less polar isomer (example 8b) having a m.p. 176°–8°.

EXAMPLE 9

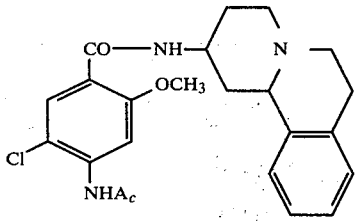

4-Acetylamino-5-chloro-N-[2-(2H-benzo[a]-quinolizine-1,3,4,6,7,11b-hexahydro)]-2-methoxy-benzamide By a procedure similar to that described in example 1, from 1,3,4,6,7,11b-hexahydro-benzo[a]-quinolizin-2-one, one isomer of 4-acetylamino-5-chloro-N-[2-(2H-benzo[a]-quinolizine-1,3,4,6,7,11b-hexahydro)]-2-methoxy-benzamide was obtained as an oil.

EXAMPLE 10

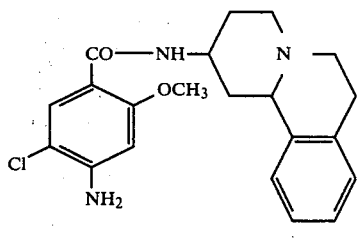

4-Amino-5-chloro-N-[2-(2H-benzo[a]-quinolizine-1,3,4,6,7,11b-hexahydro)]-2-methoxy-benzamide By a procedure similar to that described in example 2, the compound of example 9 was hydrolysed to give one isomer of 4-amino-5-chloro-N-[2-(2H-benzo[a]-quinolizine-1,3,4,6,7,11b-hexahydro)]-2-methoxy-benzamide (89%), m.p. 146°–8° after recrystallisation from ethyl acetate.

EXAMPLE 11

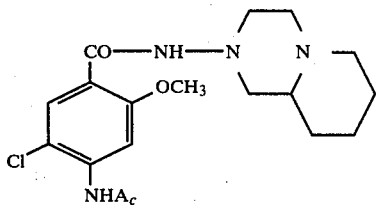

4-Acetylamino-5-chloro-2methoxy-N-(2-pyrido-[1,2-a]-pyrazinyl)-benzamide

Octahydropyrido-[1,2-a]-pyrazine (5 g) was dissolved in hydrochloric acid (5 N, 16 ml) and sodium nitrate (2.7 g) in water (10 ml) added dropwise at 0°. The solution was then heated at 60° for 30 minutes and stood at room temperature for 3 hours. It was basified, saturated with potassium carbonate and extracted with ether. The ethereal extract was dried and evaporated to give N-nitroso-octahydropyrido-[1,2-a]-pyrazine as an oil.

The N-nitroso compound (3 g) was dissolved in anhydrous THF (100 ml) and added dropwise with stirring to lithium hydride (0.7 g) in anhydrous THF (100 ml) at 55°–60° over 15 minutes. The mixture was cooled and worked up in the usual manner to give crude N-amino-octahydropyrido-[1,2-a]-pyrazine (3 g) as an oil. This was reacted with 4-acetylamino-5-chloro-2-methoxy-benzoyl chloride in the manner described in example 1 to give 4-acetylamino-5-chloro-2-methoxy-N-(2-octahydropyrido-[1,2-a]-pyrazinyl)-benzamide (67%), m.p. 200°–1° after recrystallisation from ethyl acetate-light petroleum.

EXAMPLE 12

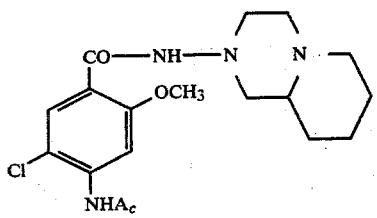

4-Amino-5-chloro-2-methoxy-N-(2-pyrido-[1,2-a]-pyrazinyl)-benzamide

By a procedure similar to that described in example 2, the compound of example 11 was hydrolysed to give 4-amino-5-chloro-2-methoxy-N-(2-octahydro-pyrido-[1,2-a]-pyrazinyl)-benzamide (65%), m.p. 118°–9°, after recrystalisation from ethyl acetate-light petroleum.

EXAMPLE 13

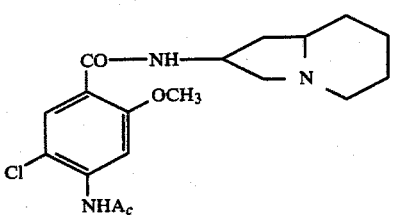

4-Acetylamino-5-chloro-2-methoxy-N-(2-octahydroindolizinyl)-benzamide

By a procedure similar to that described in example 1, from 2-keto-octahydro-indolizine, one of the isomers of 4-acetylamino-5-chloro-2-methoxy-N-(2-octahydro-indolizinyl)-benzamide, m.p. 151°–3° then 178°–9°, was obtained after recrystallisation from ethyl acetate-light petroleum.

EXAMPLE 14

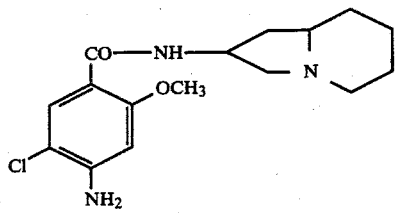

4-Amino-5-chloro-2-methoxy-N-(2-octahydroindolizinyl)-benzamide.

By a procedure similar to that described in example 2, the compound of example 13 was hydrolysed to give one of the isomers of 4-amino-5-chloro-2-methoxy-N-(2-octahydro-indolizinyl)-benzamide, m.p. 192°–3°, after recrystallisation from ethyl acetate-light petroleum.

EXAMPLE 15

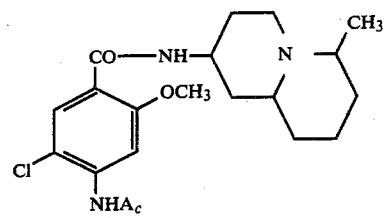

4-Acetylamino-5-chloro-2-methoxy-N-(6methyl-2-quinolizidinyl)-benzamide

By a procedure similar to that described in example 1, from 6-methyl-2-quinolizidone, a mixture of isomers of 4-acetylamino-5-chloro-2-methoxy-N-(6-methyl-6-quinolizidinyl)-benzamide was obtained as a colourless oil (93%). A partial separation of isomers was obtained by ether trituration to give a white solid [A] (43%), m.p. 205°–12° (dec.), and from the other solution, a colourless oil [B], (50%), consisting of a mixture of isomers.

EXAMPLE 16

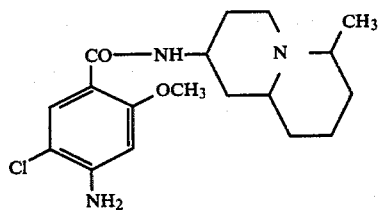

4-Amino-5-chloro-2-methoxy-N-(6-methyl-2-quinolizidinyl)-benzamide

By a procedure similar to that described in example 2, the oil [B] from example 15 was hydrolysed to give one of the isomers of 4-amino-5-chloro-2-methoxy-N-(6-methyl-2-quinolizidinyl)-benzamide (20%), m.p. 242°–3° on ether trituration and recrystallisation from chloroform/hexane.

EXAMPLE 17

4-Amino-5-chloro-2-methoxy-N-(6-methyl-2-quinolizidinyl)-benzamide

By a procedure similar to that described in example 2, the solid [A] obtained from example 15 was hydrolysed to give one of the isomers of 4-amino-5-chloro-2-methoxy-N-(6-methyl-2-quinolizidinyl)-benzamide (40%) mp=204° on ether trituration and re-crystallisation from chloroform/hexane.

Pharmacological Data

1. Compounds prepared in the Examples were tested for the following pharmacological activities in the rat:
   (a) Increase in intragastric pressure
   Intragastric pressure changes were recorded from previously starved conscious and restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the administration of the Compounds. Student "t" test was applied to the difference in average values obtained for spontaneous and post Compound activity.

(b) Increase in gastric emptying-reversal of apomorphine induced delay in gastric emptying of a test meal.

Rats equipped with chronic gastric fistula were used and it was through this that 5 ml of a test meal (5 ml phosphate buffer at pH 9) was administered and recovered. The % recovery of the standard meal after remaining in the stomach for 10 minutes was taken as an index of gastric emptying. Delay in gastric emptying was induced by the administration of Apomorphine HCl (5 mg/kg subcutaneously) and was given 15 minutes prior to the administration of the Compound. The % recoveries of the test meal was determined at 15–25 and 45–55 minutes post dosing with the Compound and compared with vehicle only dosed animals set up simultaneously. Six animals were used for each group.

(c) Inhibition of stereotype behaviour induced by apomorphine.

This is indicative of dopamine receptor blockade in the central nervous system.

The method of Ernst A. M. (1967) Pyschopharmocologia (Berl.) 10 pp. 316–323 was followed.

2. Compounds were also tested for abolition of the emetic response to apomorphine hydrochloride (0.1 mg/kg subcutaneously) in the dog The table below shows active doses (mg/kg) in these tests either by the subcutaneous (S.C.) or oral (P.O.) route of administration.

None of the compounds tested showed any signs of toxicity at the active doses.

| Compound of Example No: | Increase in Intra-Gastric Pressure | Increase in Gastric Emptying | Inhibition of Stereo-Type Behaviour | Anti-Emetic ED 50 |
|---|---|---|---|---|
| 2 | 2.5mg S.C. 50 mg P.O. | 25mg S.C. | 15mg S.C. | 0.7mg S.C. |
| 4 | 5mg S.C. | 50mg S.C. | 50mg S.C. (4 out of 7 rats) | <2mg S.C. |
| 6 | — | — | 50mg S.C. (3 out of 7 rats) | 1.4mg S.C. |
| 8b | — | — | 50mg S.C. | <2mg S.C. |
| 10 | — | 50mg S.C. | — | — |
| 12 | — | — | — | 2mg S.C. |
| 14 | — | 50mg S.C. | 50mg S.C. | <2mg S.C. |
| 16 | 1 mg S.C. | | | |

CHARACTERISING DATA

Nuclear Magnetic Resonance Data

All spectra were recorded in deuterochloroform as solvent and chemical shifts are quoted in γ units.

EXAMPLE 2

1.93 (1H,s,aromatic-6-$\underline{H}$), 2.43(1H,d,J=7 Hz, CON$\underline{H}$), 3.68(1H,s,aromatic-3-$\underline{H}$), 5.37(2H,s,N$\underline{H}_2$), 6.16(3H,s, OC$\underline{H}_3$) superimposed on broad multiplet at ca 6.0(1H,m, CONH—⟨H⟩), 7.0–9.0(15H,m,remaining-$\underline{H}$)

EXAMPLE 4

1.92(1H,s,aromatic-6-$\underline{H}$), 2.40(1H,d,J=7 Hz, CON$\underline{H}$), 3.68(1H,s,aromatic-3-$\underline{H}$), 5.42(2H,s,N$\underline{H}_2$), 6.15(3H,s,OC$\underline{H}_3$) superimposed on broad multiplet at ca 6.0(1H,m, CONH—⟨H⟩), 6.75–9.0(13H,m,remaining-$\underline{H}$).

EXAMPLE 6

1.96(1H,s,aromatic-6-$\underline{H}$), 2.55(1H,d,J=7 Hz,CON$\underline{H}$), 3.70 (1H,s,aromatic-3-$\underline{H}$), 5.33(2H,s,N$\underline{H}_2$), 6.14(3H,s,OC$\underline{H}_3$) superimposed on broad multiplet at ca 5.8(1H,m,, CONH—⟨H⟩), 6.7–9.0(15H,m,remaining-$\underline{H}$)

EXAMPLE 8b 1.96(1H,s,aromatic-6-$\underline{H}$), 1.70 (1H,broad s, CON$\underline{H}$), 3.67 (1H,s,aromatic-3-$\underline{H}$), 5.45(2H,s,N$\underline{H}_2$), 6.10(3H,s,OC$\underline{H}_3$) superimposed on broad multiplet at ca 5.9(1H,m, CONH—⟨H⟩), 7.0–8.8 (15H,m,remaining-$\underline{H}$)

EXAMPLE 8a 1.95(1H,s,aromatic-6-$\underline{H}$), 2.58(1H,d,J=7 Hz, CON$\underline{H}$), 3.65(1H,s,aromatic-3-$\underline{H}$), 5.31(2H,s,N$\underline{H}_2$), 6.11 (3H,s, OC$\underline{H}_3$) superimposed on broad multiplet at ca 6.1(1H,m, CONH—⟨H⟩), 7.0–8.9(15H,m,remaining-$\underline{H}$).

EXAMPLE 10

1.90(1H,s,aromatic-6-$\underline{H}$), 2.35(1H,d,J=7 Hz, CON$\underline{H}$), 2.7–3.1(4H,m,aromatic-$\underline{H}$), 3.72(1H,s,aromatic-3-$\underline{H}$), 5.40(2H,s, N$\underline{H}_2$), 5.70(1H,m, CONH—⟨H⟩), 6.22 (3H,s, OC$\underline{H}_3$), 6.55–9.00 (11H,m,remaining-$\underline{H}$).

EXAMPLE 12

1.97(1H,s,aromatic-6-H), 1.61(1H,s,CONH), 3.60(1H,s,aromatic-3-H), 5.10(2H,s, NH$_2$), 6.14(3H,s, OCH$_3$), 6.7-9.0 (15H,m,remaining-H)

EXAMPLE 14

2.12(1H,s,aromatic-6-H), 1.26(1H,d,J=6 Hz, CONH), 3.54(1H,s,aromatic-3-H), 4.74 (2H,s, NH$_2$),

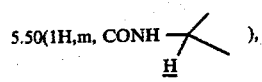

6.08(3H,s,OCH$_3$), 6.3-9.0 (13H,m,remaining-H).

EXAMPLE 16

1.93(1H,s,aromatic-6-H), 2.0(1H,broad s, CONH), 3.68 (1H,s,aromatic-3-H), 5.4-5.8 (3H,broad m, NH$_2$ and

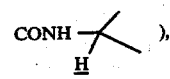

6.06 (3H,s,OCH$_3$).

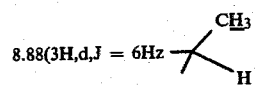

superimposed on broad multiplets at 6.7-9.0 (14H,m,remaining-H)

EXAMPLE 17

1.90(1H,s,aromatic-6-H), 2.40(1H,d,J=7 Hz, CONH), 3.66(1H,s,aromatic-3-H), 5.4 (2H,broad s, NH$_2$), 6.15(3H,s, OCH$_3$) superimposed on broad multiplet at ca

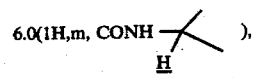

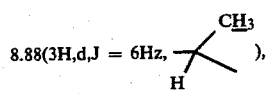

6.3-9.2(14H m, remaining-H)

What we claim is:

1. A compound of the formula (I),

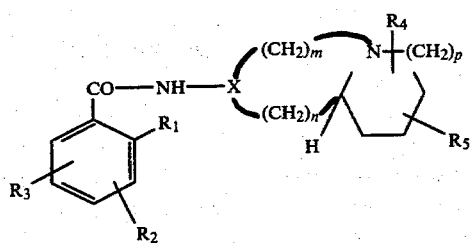

or a pharmaceutically acceptable salt thereof wherein
$R_1$ is alkoxy of 1 to 6 carbon atoms;
$R_2$ and $R_3$ are the same or different and are hydrogen, halogen, $CF_3$, hydroxy, alkoxy of 1 to 6 carbon atoms, alkanoyl of 2 to 7 carbon atoms, amino, amino substituted by one or two alkyl moieties of 1 to 6 carbon atoms, alkanoylamino of 2 to 7 carbon atoms, aminocarbonyl or aminosulphone unsubstituted or substituted by one or two alkyl moieties of 1 to 6 carbon atoms, alkylsulphone of 1 to 6 carbon atoms or nitro;
X is either a nitrogen atom, in which case m+n is 3 to 5, m is 2 to 4, and n is 1 to 3; or X is CH in which case m+n is 2 to 5, m is 1 to 5, and n is 0 to 4;
P is 0 to 3;
$R_4$ is hydrogen, alkyl of 1 to 6 carbon atoms, phenyl or phenyl-alkyl of 1 to 6 carbon atoms in the alkyl moiety, said phenyl or phenylalkyl being nuclear-unsubstituted or nuclear-substituted by alkyl of 1 to 6 carbon atoms, alkoxy of 1 to 6 carbon atoms, $CF_3$ or halogen, and $R_5$ is hydrogen; or $R_4$ and $R_5$ are attached to two adjacent carbon atoms and form together with these two carbon atoms a fused benzene ring, which benzene ring is unsubstituted or substituted by alkyl of 1 to 6 carbon atoms, alkoxy of 1 to 6 carbon atoms, $CF_3$ or halogen.

2. A compound according to claim 26, wherein
$R_1$ is alkoxy of 1 to 6 carbon atoms;
$R_2$ and $R_3$ are the same or different and are hydrogen, halogen, $CF_3$, hydroxy, alkoxy of 1 to 6 carbon atoms, alkanoyl of 2 to 7 carbon atoms, amino, amino substituted by one or two alkyl moieties of 1 to 6 carbon atoms, alkanoylamino of 2 to 7 carbon atoms, aminosulphone, aminosulphone substituted by one or two alkyl moieties of 1 to 6 carbon atoms, alkylsulphone of 1 to 6 carbon atoms or nitro;
m+n is 2 or 3, and m is 1, 2 or 3 and n is 0, 1 or 2;
P is 0 or 1;
$R_4$ is hydrogen, alkyl of 1 to 6 carbon atoms, phenyl or phenyl-alkyl of 1 to 6 carbon atoms in the alkyl moiety, said phenyl or said phenyl-alkyl being nuclear-unsubstituted or nuclear-substituted by alkyl of 1 to 6 carbon atoms, alkoxy of 1 to 6 carbon atoms, $CF_3$ or halogen, and $R_5$ is hydrogen; or $R_4$ and $R_5$ are attached to two adjacent carbon atoms and form together with these two carbon atoms a fused benzene ring, which benzene ring is unsubstituted or substituted by alkyl of 1 to 6 carbon atoms, alkoxy of 1 to 6 carbon atoms, $CF_3$ or halogen.

3. A compound according to claim 1 wherein $R_2$ is 4-amino and $R_3$ is hydrogen or 5-halo.

4. A compound according to claim 3, wherein $R_3$ is 5-chloro.

5. A compound according to claim 3 wherein $R_1$ is methoxy.

6. A compound according to claim 1, wherein the moiety of the formula (IV):

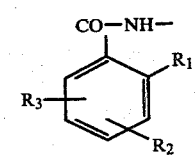

in the compound of formula (I) has the structure (V):

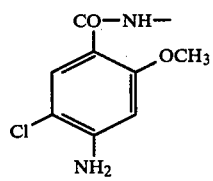

(V)

7. A compound according to claim 6, wherein the moiety of the formula (VI):

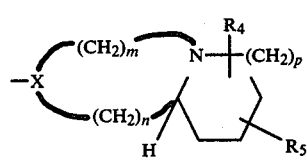

in the compound of formula (I) has the structure (XI):

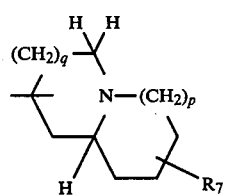

wherein q is 0 to 3, p is 0 to 3, and $R_7$ is hydrogen, alkyl of 1 to 6 carbon atoms, phenyl or phenyl-alkyl of 1 to 6 carbon atoms in the alkyl moiety, said phenyl or said phenyl-alkyl being nuclear-unsubstituted or nuclear-substituted by alkyl of 1 to 6 carbon atoms, alkoxy of 1 to 6 carbon atoms, $CF_3$ or halogen.

8. A compound according to claim 7, wherein q is 0 or 1 and p is 0 or 1.

9. A compound according to claim 8, wherein q is 1 and p is 1.

10. A compound according to claim 9, wherein the moiety of formula (XI) is 4-substituted by the moiety of the formula (V)

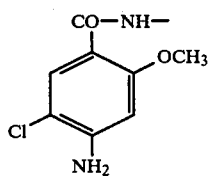

(V)

11. A compound according to claim 8 wherein $R_7$ is hydrogen.

12. A compound according to claim 7, wherein the moiety of the formula (VI) is of the formula (XII), (XIII), or (XIV):

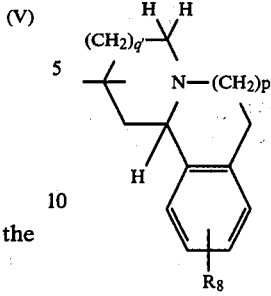

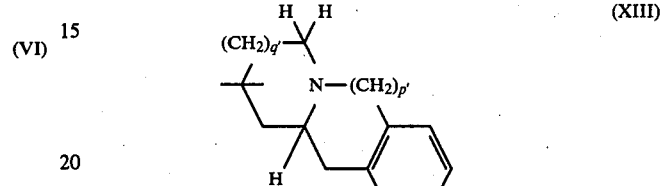

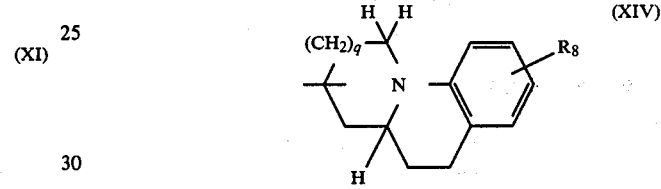

wherein q' is 0 or 1, p' is 0 or 1 and $R_8$ is hydrogen, alkyl of 1 to 6 carbon atoms, alkoxy of 1 to 6 carbon atoms, $CF_3$ or halogen.

13. A compound according to claim 12, wherein p' and q' are both 1.

14. A compound according to claim 13, wherein $R_8$ is hydrogen.

15. A compound according to claim 7, wherein the moiety of the formula (VI) is of the formula (VII):

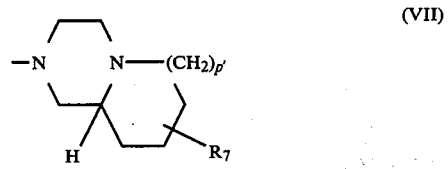

wherein p' is 0 or 1, and $R_7$ is hydrogen, alkyl of 1 to 6 carbon atoms, phenyl or phenyl-alkyl of 1 to 6 carbon atoms, said phenyl or said phenyl-alkyl being nuclear-unsubstituted or nuclear-substituted by alkyl of 1 to 6 carbon atoms, alkoxy of 1 to 6 carbon atoms, $CF_3$ or halogen.

16. A compound according to claim 15, wherein $R_7$ is hydrogen.

17. A compound according to claim 16, wherein p' is 1.

18. A compound according to claim 7, wherein the moiety of the formula (VI) is of the formula (VIII), (IX), or (X):

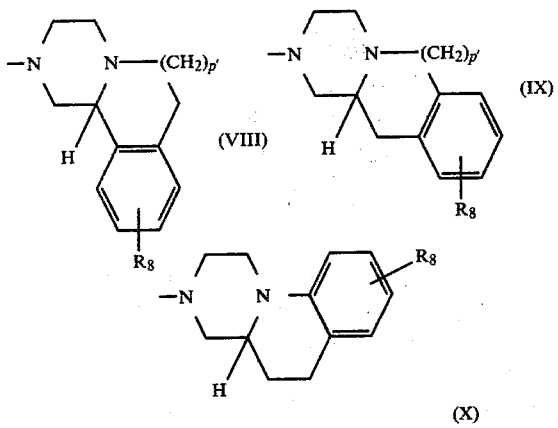

wherein p' is 0 or 1, $R_8$ is hydrogen, alkyl of 1 to 6 carbon atoms alkoxy of 1 to 6 carbon atoms $CF_3$ or halogen.

19. A compound according to claim 18, wherein $R_8$ is hydrogen.

20. A compound according to claim 18 wherein p' is 1.

21. A compound according to claim 1 wherein X is CH wherein m+n is 2 to 5, m is 1 to 5 and n is 0 to 4.

22. A compound according to claim 1 wherein X is CH wherein m+n is 2 to 4, m is 1 to 4 and n is 0 to 3.

23. The compound according to claim 1 which is 4-Acetylamino-0-chloro-2-methoxy-N-(2-quinolizidinyl)-benzamide.

24. The compound according to claim 1 which is 4-Amino-5-chloro-2-methoxy-N-(2-quinolizidinyl)-benzamide.

25. The compound according to claim 1 which is 4-Acetylamino-5-chloro-2-methoxy-N-(7-octahydro-indolizinyl)-benzamide.

26. The compound according to claim 1 which is 4-Amino-5-chloro-2-methoxy-N-(7-octahydro-indolizinyl)-benzamide.

27. The compound according to claim 1 which is 4-Acetylamino-5-chloro-2-methoxy-N-(3-quinolizidinyl)-benzamide.

28. The compound according to claim 1 which is 4-Amino-5-chloro-2-methoxy-N-(3-quinolizidinyl)-benzamide.

29. The compound according to claim 1 which is 4-Acetylamino-5-chloro-2-methoxy-N-(1-quinolizidinyl)-benzamide.

30. The compound according to claim 1 which is 4-Amino-5-chloro-2-methoxy-N-(1-quinolizidinyl)-benzamide.

31. The compound according to claim 1 which is 4-Acetylamino-5-chloro-N-[2-(2H-benzo[a]-quinolizine-1,3,4,6,7,11b-hexahydro)]-2-methoxy-benzamide.

32. The compound according to claim 1 which is 4-Amino-5-chloro-N-[2-(2H-benzo[a]-quinolizine-1,3,4,6,7,11b-hexahydro)]-2-methoxy-benzamide.

33. The compound according to claim 1 which is 4-Acetylamino-5-chloro-2-methoxy-N-(pyrido-[1,2a]-pyrazinyl)-benzamide.

34. The compound according to claim 1 which is 4-Amino-5-chloro-2-methoxy-N-(2-pyrido-[1,2-a]-pyrazinyl)-benzamide.

35. The compound according to claim 1 which is 4-Acetylamino-5-chloro-2-methoxy-N-(2-octahydroindolizinyl)-benzamide.

36. The compound according to claim 1 which is 4-Amino-5-chloro-2-methoxy-N-(2-octahydroinodolizinyl)-benzamide.

37. The compound according to claim 1 which is 4-Acetylamino-5-chloro-2-methoxy-N-(6-methyl-2-quinolizidinyl)-benzamide.

38. The compound according to claim 1 which is 4-Amino-5-chloro-2-methoxy-N-(6-methyl-2-quinolizidinyl)-benzamide.

39. The compound according to claim 1 which is a diastereomer of 4-Amino-5-chloro-2-methoxy-N-(6-methyl-2-quinolizidinyl)-benzamide.

40. The diastereomer of 4-Amino-5-chloro-2-methoxy-N-(6-methyl-2-quinolizidinyl)-benzamide of claim 39 having a melting point of 242° C. to 243° C.

41. The diastereomer of 4-Amino-5-chloro-2-methoxy-N-(6-methyl-2-quinolizidinyl)-benzamide of claim 39 having a melting point of 204° C.

42. The compound according to claim 24 which is a diastereomer of 4-Amino-5-chloro-2-methoxy-N-(2-quinolizidinyl)-benzamide.

43. The diastereomer of 4-Amino-5-chloro-2-methoxy-N-(2-quinolizidinyl)-benzamide according to claim 42 having a 1H n.m.r. spectrum in deuterochloroform, containing the following resonances in γ units:

1.93 (1H, s), 2.43 (1H, d, J=7Hz),
3.68 (1H, s), 6.16 (3H, s),
6.0 (1H, m), 7.0–9.0 (15H, m).

44. A pharmaceutical composition useful for the treatment of disorders of the gastro-intestinal function and emesis which comprises a therapeutically effective amount of a compound of the formula (I)

$$\text{(I)}$$

or a pharmaceutically acceptable salt thereof wherein
$R_1$ is alkoxy of 1 to 6 carbon atoms;
$R_2$ and $R_3$ are the same or different and are hydrogen, halogen, $CF_3$, hydroxy, alkoxy of 1 to 6 carbon atoms, alkanoyl of 2 to 7 carbon atoms, amino, amino substituted by one or two alkyl moieties of 1 to 6 carbon atoms, alkanoylamino of 2 to 7 carbon atoms, aminocarbonyl or aminosulphone unsubstituted or substituted by one or two alkyl moieties of 1 to 6 carbon atoms, alkylsulphone of 1 to 6 carbon atoms or nitro;
X is either a nitrogen atom, in which case m+n is 3 to 5, m is 2 to 4 and n is 1 to 3; or X is CH in which case m+n is 2 to 5, m is 1 to 5, and n is 0 to 4;
p is 0 to 3;
$R_4$ is hydrogen, alkyl of 1 to 6 carbon atoms, phenyl or phenyl-alkyl of 1 to 6 carbon atoms in the alkyl moiety, said phenyl or phenyl-alkyl being nuclear-unsubstituted or nuclear substituted by alkyl of 1 to 6 carbon atoms, alkoxy of 1 to 6 carbon atoms, CF₃ or halogen, and R₅ is hydrogen; or R₄ and R₅ are attached to two adjacent carbon atoms and form together with these two adjacent carbon atoms, a fused benzene ring, which benzene ring is unsubstituted or substituted by alkyl of 1 to 6 carbon atoms, alkoxy of 1 to 6 carbon atoms, CF₃ or halogen, in combination with a pharmaceutically acceptable carrier.

45. A composition according to claim 44 wherein R₁ is alkoxy of 1 to 6 carbon atoms;

R₂ and R₃ are the same or different and are hydrogen, halogen, CF₃, hydroxy, alkoxy of 1 to 6 carbon atoms, alkanoyl of 2 to 7 carbon atoms, amino, amino substituted by one or two alkyl moieties of 1 to 6 carbon atoms, alkanoylamino or 2 to 7 carbon atoms, aminosulphone, aminosulphone substituted by one or two alkyl moieties of 1 to 6 carbon atoms, alkylsulphone of 1 to 6 carbon atoms or nitro, m+n is 2 or 3, and m is 1, 2 or 3 and n is 0, 1 or 2; p is 0 or 1;

R₄ is hydrogen, alkyl of 1 to 6 carbon atoms, phenyl or phenyl-alkyl of 1 to 6 carbon atoms in the alkyl moiety, said phenyl or said phenyl-alkyl being nuclear-unsubstituted or nuclear-substituted by alkyl of 1 to 6 carbon atoms, alkoxy of 1 to 6 carbon atoms, CF₃ or halogen, and R₅ is hydrogen; or R₄ and R₅ are attached to two adjacent carbon atoms and form together with these two carbon atoms a fused benzene ring, which benzene ring is unsubstituted or substituted by alkyl of 1 to 6 carbon atoms, alkoxy of 1 to 6 carbon atoms, CF₃ or halogen.

46. A composition according to claim 44 wherein R₂ is 4-amino and R₃ is hydrogen or 5-halo.

47. A composition according to claim 46 wherein R₃ is 5-chloro.

48. A composition according to claim 46 wherein R₁ is methoxy.

49. A composition according to claim 44 wherein the moiety of the formula (IV):

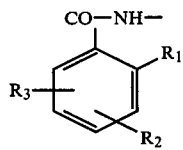

in the compound of formula (I) has the structure (V):

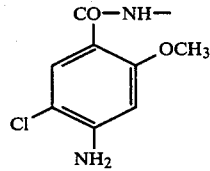

50. A composition according to claim 49 wherein the moiety of formula (VI):

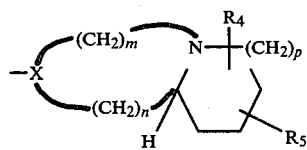

in the compound of formula (I) has the structure (XI):

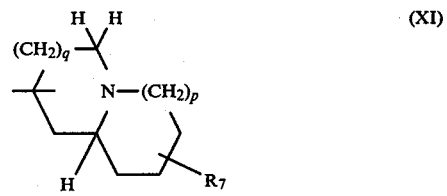

wherein q is 0 to 3, p is 0 to 3, and R₇ is hydrogen, alkyl of 1 to 6 carbon atoms, phenyl or phenyl-alkyl of 1 to 6 carbon atoms in the alkyl moiety, said phenyl or said phenyl-alkyl being nuclear-unsubstituted or nuclear-substituted by alkyl of 1 to 6 carbon atoms, alkoxy of 1 to 6 carbon atoms, CF₃ or halogen.

51. A composition according to claim 50, wherein q is 0 to 1 and p is 0 or 1.

52. A composition according to claim 51 wherein q is 1 and p is 1.

53. A composition according to claim 52 wherein the moiety of formula (XI) is 4-substituted by the moiety of the formula (V)

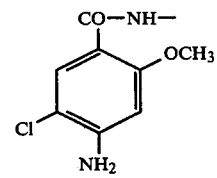

54. A composition according to claim 51 wherein R₇ is hydrogen.

55. A composition according to claim 50 wherein the moiety of the formula (VI) is of the formula (XII), (XIII), or (XIV):

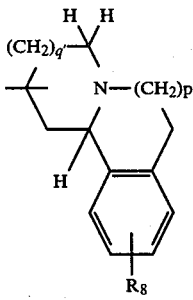

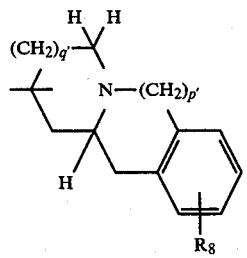

-continued $$\text{(XIV)}$$

(structure: bicyclic amine with (CH$_2$)$_q$ bridge, N, and fused benzene ring bearing R$_8$)

wherein q' is 0 or 1, p' is 0 or 1 and R$_8$ is hydrogen, alkyl of 1 to 6 carbon atoms, alkoxy of 1 to 6 carbon atoms, CF$_3$ or halogen.

56. A composition according to claim 55 wherein p' and q' are both 1.

57. A composition according to claim 56 wherein R$_8$ is hydrogen.

58. A composition according to claim 44 wherein X is CH wherein m+n is 2 to 5, m is 1 to 5 and n is 0 to 4.

59. A composition according to claim 44 wherein X is CH wherein m+n is 2 to 4, m is 1 to 4 and n is 0 to 3.

60. A composition according to claim 44 wherein the compound is 4-Acetylamino-5-chloro-2-methoxy-N-(2-quinolizidinyl)-benzamide.

61. A composition according to claim 44 wherein the compound is 4-Amino-5-chloro-2-methoxy-N-(2-quinolizidinyl)-benzamide.

62. A composition according to claim 44 wherein the compound is 4-Acetylamino-5-chloro-2-methoxy-N-(7-octahydro-indolizinyl)-benzamide.

63. A composition according to claim 44 wherein the compound is 4-Amino-5-chloro-2-methoxy-N-(7-octahydro-indolizinyl)-benzamide.

64. A composition according to claim 44 wherein the compound is 4-Acetylamino-5-chloro-2-methoxy-N-(3-quinolizidinyl)-benzamide.

65. A composition according to claim 44 wherein the compound is 4-Amino-5-chloro-2-methoxy-N-(3-quinolizidinyl)-benzamide.

66. A composition according to claim 44 wherein the compound is 4-Acetylamino-5-chloro-2-methoxy-N-(1-quinolizidinyl)-benzamide.

67. A composition according to claim 28 wherein the compound is 4-Amino-5-chloro-2-methoxy-N-(1-quinolizidinyl)-benzamide.

68. A composition according to claim 44 wherein the compound is 4-Acetylamino-5-chloro-N-[2-(2H-benzo[a]-quinolizine-1,3,4,6,7,11b-hexahydro)]2-methoxy-benzamide.

69. A composition according to claim 44 wherein the compound is 4-Amino-5-chloro-N-[2-(2H-benzo[a]-quinolizine-1,3,4,6,7,11b-hexahydro)]-2-methoxy-benzamide.

70. A composition according to claim 44 wherein the compound is 4-Acetylamino-5-chloro-2-methoxy-N-(pyrido-[1,2-a]-pyrazinyl)-benzamide.

71. A composition according to claim 44 wherein the compound is 4-Amino-5-chloro-2-methoxy-N-(2-pyrido-[1,2-a]-pyrazinyl)-benzamide.

72. A composition according to claim 44 wherein the compound is 4-Acetylamino-5-chloro-2-methoxy-N-(2-octahydroindolizinyl)-benzamide.

73. A composition according to claim 44 wherein the compound is 4-Amino-5-chloro-2-methoxy-N-(2-octahydroinodolizinyl)-benzamide.

74. A composition according to claim 28 wherein the compound 4-Acetylamino-5-chloro-2-methoxy-N-(6-methyl-2-quinolizinyl)-benzamide.

75. A composition according to claim 44 wherein the compound is 4-Amino-5-chloro-2-methoxy-N-(6-methyl-2-quinolizidinyl)-benzamide.

76. The compound according to claim 44 wherein the compound is a diastereomer of 4-Amino-5-chloro-2-methoxy-N-(6-methyl-2-quinolizidinyl)-benzamide.

77. A composition according to claim 76 wherein the compound is the diastereomer of 4-Amino-5-chloro-2-methoxy-N-(6-methyl-2-quinolizidinyl)-benzamide, having a melting point of 242° C. to 243° C.

78. A composition according to claim 76 wherein the compound is the diastereomer of 4-Amino-5-chloro-2-methoxy-N-(6-methyl-2-quinolizidinyl)-benzamide, having a melting point of 204° C.

79. A composition according to claim 61 wherein the compound is a diastereomer of 4-Amino-5-chloro-2-methoxy-N-(2-quinolizidinyl)-benzamide.

80. A composition according to claim 79 wherein the compound is the diastereomer of 4-Amino-5-chloro-2-methoxy-N-(2-quinolizidinyl)-benzamide according to claim 42 having a 1H n.m.r. spectrum in deuterochloroform, containing the following resonances in γ units:

1.93 (1H, s), 2.43 (1H, d, J=7 Hz),
3.68 (1H, s), 6.16 (3H, s),
6.0 (1H, m), 7.0–9.0 (15H, m).

81. A method of treating disorders of the gastro-intestinal function and emesis in humans and animals which comprises administering to a human or animal in need thereof a therapeutically effective amount of a compound of the formula (I)

$$\text{(I)}$$

(structure showing substituted benzamide with R$_1$, R$_2$, R$_3$ on aromatic ring, CO—NH—X linker, (CH$_2$)$_m$ and (CH$_2$)$_n$ bridges to N with (CH$_2$)$_p$, R$_4$, R$_5$)

or a pharmaceutically acceptable salt thereof wherein
R$_1$ is alkoxy of 1 to 6 carbon atoms;
R$_2$ and R$_3$ are the same or different and are hydrogen, halogen, CF$_3$, hydroxy, alkoxy of 1 to 6 carbon atoms, alkanoyl of 2 to 7 carbon atoms, amino, amino substituted by one or two alkyl moieties of 1 to 6 carbon atoms, alkanoylamino of 2 to 7 carbon atoms, aminocarbonyl or aminosulphone unsubstituted or substituted by one or two alkyl moieties of 1 to 6 carbon atoms, alkylsulphone of 1 to 6 carbon atoms or nitro;
X is either a nitrogen atom, in which case m+n is 3 to 5, m is 2 to 4 and n is 1 to 3; or X is CH in which case m+n is 2 to 5, m is 1 to 5, and n is 0 to 4;
p is 0 to 3;
R$_4$ is hydrogen, alkyl of 1 to 6 carbon atoms, phenyl or phenyl-alkyl of 1 to 6 carbon atoms in the alkyl moiety, said phenyl or phenyl-alkyl being nuclear-unsubstituted or nuclear substituted by alkyl of 1 to 6 carbon atoms, alkoxy of 1 to 6 carbon atoms, CF$_3$ or halogen, and R$_5$ is hydrogen; or R$_4$ and R$_5$ are attached to two adjacent carbon atoms and form together with these two adjacent carbon atoms, a fused benzene ring, which benzene ring is unsubstituted or substituted by alkyl of 1 to 6 carbon atoms, alkoxy of 1 to 6 carbon atoms, $CF_3$ or halogen, in combination with a pharmaceutically acceptable carrier.

82. A method according to claim 81 wherein
$R_1$ is alkoxy of 1 to 6 carbon atoms;
$R_2$ and $R_3$ are the same or different and are hydrogen, halogen, $CF_3$, hydroxy, alkoxy of 1 to 6 carbon atoms, alkanoyl of 2 to 7 carbon atoms, amino, amino substituted by one or two alkyl moieties of 1 to 6 carbon atoms, alkanoylamino or 2 to 7 carbon atoms, aminosulphone, aminosulphone substituted by one or two alkyl moieties of 1 to 6 carbon atoms, alkysulphone of 1 to 6 carbon atoms or nitro, m+n is 2 or 3, and m is 1, 2 or 3 and n is 0, 1 or 2;
p is 0 or 1;
$R_4$ is hydrogen, alkyl of 1 to 6 carbon atoms, phenyl or phenyl-alkyl of 1 to 6 carbon atoms in the alkyl moiety, said phenyl or said phenyl-alkyl being nuclear-unsubstituted or nuclear-substituted by alkyl of 1 to 6 carbon atoms, alkoxy of 1 to 6 carbon atoms, $CF_3$ or halogen, and $R_5$ is hydrogen; or $R_4$ and $R_5$ are attached to two adjacent carbon atoms and form together with these two carbon atoms a fused benzene ring, which benzene ring is unsubstituted or substituted by alkyl of 1 to 6 carbon atoms, alkoxy of 1 to 6 carbon atoms, $CF_3$ or halogen.

83. A method according to claim 81 wherein $R_2$ is 4-amino and $R_3$ is hydrogen or 5-halo.

84. A method according to claim 83 wherein $R_3$ is 5-chloro.

85. A method according to claim 83 wherein $R_1$ is methoxy.

86. A method according to claim 81 wherein the moiety of the formula (IV):

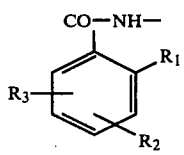

in the compound of formula (I) has the structure (V):

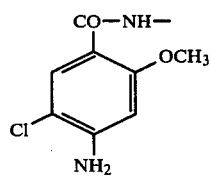

87. A method according to claim 85 wherein the moiety of formula (VI):

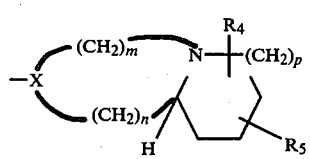

in the compound of formula (I) has the structure (XI):

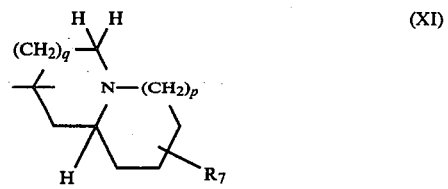

wherein q is 0 to 3, p is 0 to 3, and $R_7$ is hydrogen alkyl of 1 to 6 carbon atoms, phenyl or phenyl-alkyl of 1 to 6 carbon atoms in the phenyl moiety, said phenyl or said phenyl-alkyl being nuclear-unsubstituted or nuclear-substituted by alkyl of 1 to 6 carbon atoms, alkoxy of 1 to 6 carbon atoms, $CF_3$ or halogen.

88. A method according to claim 87 wherein q is 0 to 1 and p is 0 or 1.

89. A method according to claim 88 wherein q is 1 and p is 1.

90. A method according to claim 89 wherein the moiety of formula (XI) is 4-substituted by the moiety of the formula (V)

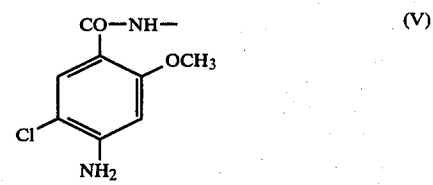

91. A method according to claim 87 wherein the moiety of the formula (VI) is of the formula (XII), (XIII), or (XIV):

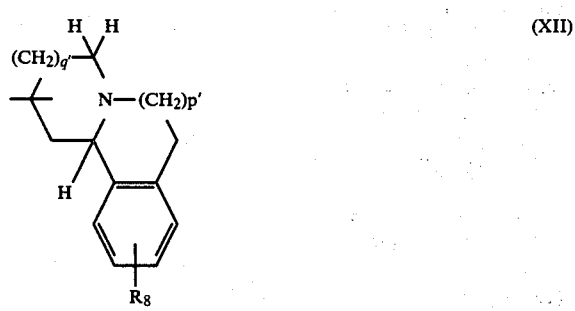

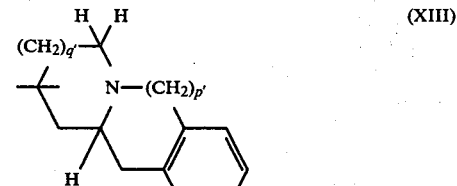

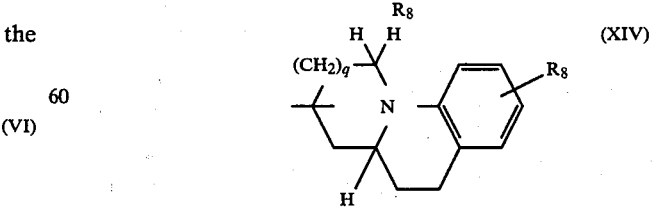

wherein q' is 0 or 1, p' is 0 or 1 and $R_8$ is hydrogen, alkyl of 1 to 6 carbon atoms, alkoxy of 1 to 6 carbon atoms, $CF_3$ or halogen.

92. A method according to claim 90 wherein p' and q' are both 1.

93. A method according to claim 90 wherein $R_8$ is hydrogen.

94. A method according to claim 81 wherein X is CH wherein m+n is 2 to 5, m is 1 to 5 and n is 0 to 4.

95. A method according to claim 81 wherein X is CH wherein m+n is 2 to 4, m is 1 to 4 and n is 0 to 3.

96. A method according to claim 81 wherein the compound is 4-Acetylamino-5-chloro-2-methoxy-N-(2-quinolizidinyl)-benzamide.

97. A method according to claim 81 wherein the compound is 4-Amino-5-chloro-2-methoxy-N-(2-quinolizidinyl)-benzamide.

98. A method according to claim 81 wherein the compound is 4-Acetylamino-5-chloro-2-methoxy-N-(7-octahydro-indolizinyl)-benzamide.

99. A method according to claim 81 wherein the compound is 4-Amino-5-chloro-2-methoxy-N-(7-octahydro-indolizinyl)-benzamide.

100. A method according to claim 81 wherein the compound is 4-Acetylamino-5-chloro-2-methoxy-N-(3-quinolizidinyl)-benzamide.

101. A method according to claim 81 wherein the compound is 4-Amino-5-chloro-2-methoxy-N-(3-quinolizidinyl)-benzamide.

102. A method according to claim 81 wherein the compound is 4-Acetylamino-5-chloro-2-methoxy-N-(1-quinolizidinyl)-benzamide.

103. A method according to claim 81 wherein the compound is 4-Amino-5-chloro-2-methoxy-N-(1-quinolizidinyl)-benzamide.

104. A method according to claim 81 wherein the compound is 4-Acetylamino-5-chloro-N-[2-(2H-benzo[a]-quinolizine-1,3,4,6,7,11b-hexahydro)]-2-methoxy-benzamide.

105. A method according to claim 81 wherein the compound is 4-Amino-5-chloro-N-[2-(2H-benzo[a]-quinolizine-1,3,4,6,7,11b-hexahydro)]-2-methoxy-benzamide.

106. A method according to claim 81 wherein the compound is 4-Acetylamino-5-chloro-2-methoxy-N-(pyrido-[1,2-a]-pyrazinyl)-benzamide.

107. A method according to claim 81 wherein the compound is 4-Amino-5-chloro-2-methoxy-N-(2-pyrido-[1,2-a]-pyrazinyl)-benzamide.

108. A method according to claim 81 wherein the compound is 4-Acetylamino-5-chloro-2-methoxy-N-(2-octahydroindolizinyl)-benzamide.

109. A method according to claim 81 wherein the compound is 4-Amino-5-chloro-2-methoxy-N-(2-octahydroinodolizinyl)-benzamide.

110. A method according to claim 81 wherein the compound is 4-Acetylamino-5-chloro-2-methoxy-N-(6-methyl-2-quinolizinyl)-benzamide.

111. A method according to claim 81 wherein the compound is 4-Amino-5-chloro-2-methoxy-N-(6-methyl-2-quinolizidinyl)-benzamide.

112. A method according to claim 81 wherein the compound is a diastereomer of 4-Amino-5-chloro-2-methoxy-N-(6-methyl-2-quinolizidinyl)-benzamide.

113. A method according to claim 112 wherein the compound is the diastereomer of 4-Amino-5-chloro-2-methoxy-N-(6-methyl-2-quinolizidinyl)-benzamide, having a melting point of 242° C. to 243° C.

114. A method according to claim 112 wherein the compound is the diastereomer of 4-Amino-5-chloro-2-methoxy-N-(6-methyl-2-quinolizidinyl)-benzamide, having a melting point of 204° C.

115. A method according to claim 97 wherein the compound is a diastereomer of 4-Amino-5-chloro-2-methoxy-N-(2-quinolizidinyl)-benzamide.

116. A method according to claim 115 wherein the compound is the diastereomer of 4-Amino-5-chloro-2-methoxy-N-(2-quinolizidinyl)-benzamide having a 1H n.m.r. spectrum in deuterocloroform, containing the following resonances in γ units:
1.93 (1H, s), 2.43 (1H, d, J=7 Hz),
3.68 (1H, s), 6.16 (3H, s),
6.0 (1H, m), 7.0–9.0 (15H, m).

* * * * *